(12) United States Patent
Bauss et al.

(10) Patent No.: US 10,653,852 B2
(45) Date of Patent: May 19, 2020

(54) MEDICAMENT DELIVERY DEVICE

(71) Applicant: SHL MEDICAL AG, Zug (CH)

(72) Inventors: Markus Bauss, Lengdorf (DE);
Christian Keller, Taipei (TW)

(73) Assignee: SHL MEDICAL AG, Zug (CH)

( * ) Notice: Subject to any disclaimer, the term of this patent is extended or adjusted under 35 U.S.C. 154(b) by 46 days.

(21) Appl. No.: 15/771,882

(22) PCT Filed: Oct. 17, 2016

(86) PCT No.: PCT/EP2016/074893
§ 371 (c)(1),
(2) Date: Apr. 27, 2018

(87) PCT Pub. No.: WO2017/071983
PCT Pub. Date: May 4, 2017

(65) Prior Publication Data
US 2018/0326164 A1 Nov. 15, 2018

(30) Foreign Application Priority Data

Oct. 28, 2015 (EP) .................................. 15191953

(51) Int. Cl.
A61M 5/50 (2006.01)
A61M 5/20 (2006.01)
A61M 5/315 (2006.01)

(52) U.S. Cl.
CPC ............ A61M 5/5086 (2013.01); A61M 5/20 (2013.01); A61M 5/2033 (2013.01);
(Continued)

(58) Field of Classification Search
CPC .......... A61M 2205/33; A61M 2205/00; A61M 2205/35; A61M 2205/3576;
(Continued)

(56) References Cited

U.S. PATENT DOCUMENTS

| 9,089,650 B2 | 7/2015 | Nielsen et al. |
| 9,289,559 B2 | 3/2016 | Pedersen et al. |
| 2011/0295215 A1* | 12/2011 | Nielsen .................. G16H 20/17 604/257 |
| 2011/0313350 A1* | 12/2011 | Krulevitch .............. A61M 5/24 604/65 |

(Continued)

FOREIGN PATENT DOCUMENTS

| CN | 102170929 A | 8/2011 |
| CN | 103458945 A | 12/2013 |

(Continued)

OTHER PUBLICATIONS

Search Report issued in Taiwanese Patent Application No. 105133900 dated Aug. 4, 2017.

Primary Examiner — Jason E Flick
(74) Attorney, Agent, or Firm — McDonnell Boehnen Hulbert & Berghoff LLP

(57) ABSTRACT

The present invention relates to a medicament delivery device comprising a housing, a power unit (24, 26, 28), said power unit comprising: an actuation element (52); which actuation element (52) is operably arranged to move inside said housing ( ) for expelling a dose of medicament; said medicament delivery device further comprising a monitoring unit (30); said monitoring unit (30) being detachably attached to said housing; at least one sensor (32, 54) arranged in said monitoring unit (30), said at least one sensor (32, 54) being operably arranged to monitor said power unit (24, 26, 28) for obtaining information regarding status of the medicament delivery device.

20 Claims, 3 Drawing Sheets

(52) U.S. Cl.
CPC ........ *A61M 5/315* (2013.01); *A61M 5/31511* (2013.01); *A61M 2205/332* (2013.01); *A61M 2205/3306* (2013.01); *A61M 2205/3584* (2013.01); *A61M 2205/3592* (2013.01); *A61M 2205/581* (2013.01); *A61M 2205/582* (2013.01); *A61M 2205/583* (2013.01)

(58) Field of Classification Search
CPC .............. A61M 2205/58; A61M 5/178; A61M 2005/2006; A61M 5/31; A61M 5/50; A61M 2205/3306; A61M 2205/332; A61M 2205/3584; A61M 2205/3592; A61M 2205/581; A61M 2205/582; A61M 2205/583; A61M 5/20; A61M 5/2033; A61M 5/315; A61M 5/31511; A61M 5/5086
USPC ......................................................... 604/111
See application file for complete search history.

(56) References Cited

U.S. PATENT DOCUMENTS

| | | | | |
|---|---|---|---|---|
| 2014/0074041 A1* | 3/2014 | Pedersen | ................. | A61M 5/20 604/211 |
| 2014/0128843 A1* | 5/2014 | Baker | .................... | A61M 5/20 604/506 |
| 2014/0378903 A1 | 12/2014 | Quinlan | | |

FOREIGN PATENT DOCUMENTS

| | | | |
|---|---|---|---|
| EP | 2190506 | B1 | 6/2010 |
| TW | 201509477 | A | 3/2015 |
| WO | 2010142598 | A2 | 12/2010 |
| WO | 2013010893 | A1 | 1/2013 |
| WO | WO-2014023763 | A1 * | 2/2014 |
| WO | 2015136564 | A1 | 9/2015 |

* cited by examiner

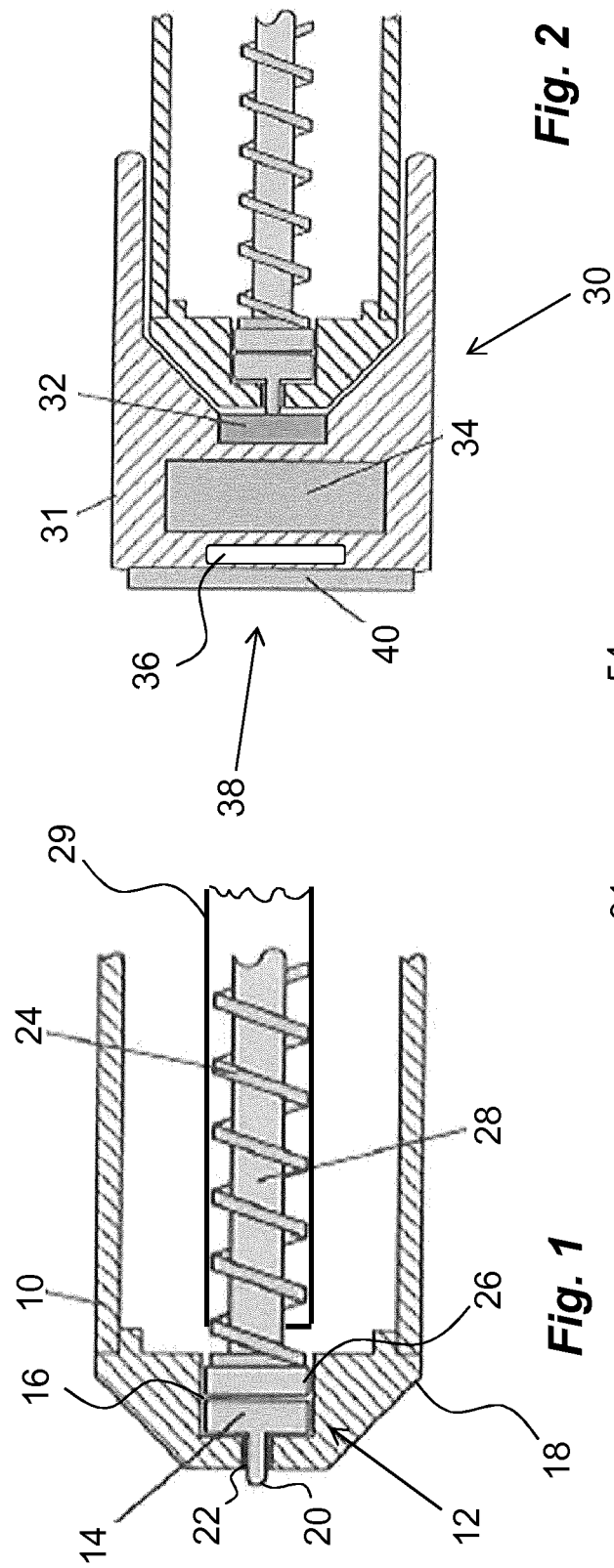
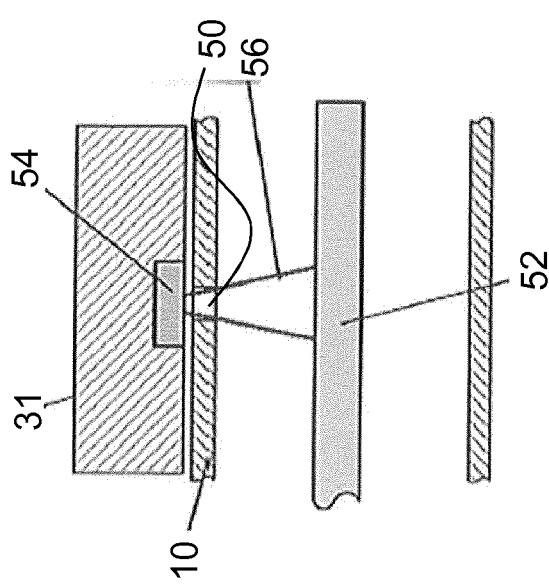
Fig. 1
Fig. 2
Fig. 3

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/074893 filed Oct. 17, 2016, which claims priority to European Patent Application No. 15191953.7 filed Oct. 28, 2015. The entire disclosure contents of these applications are hereby incorporated by reference into the present application.

TECHNICAL AREA

The present invention relates to a device for sensing forces that occur during operation of a medicament delivery device.

BACKGROUND OF INVENTION

There is an ever increasing demand for obtaining information from different devices and apparatuses that we use daily, and medicament delivery devices are no exception to that demand. Because of this, a number of medicament delivery devices have been developed that contain "smart" features such as sensor and monitoring systems, communication circuits, man-machine interfaces that can present information regarding the status of the medicament delivery device, for instance.

Even though the costs of these smart features are decreasing, it is, for instance, still too costly to provide disposable, smart medicament delivery devices. Another factor is also that the discarded medicament delivery devices would contain waste components that would be much better to recycle than to throw away, if disposable medicament delivery devices were to be provided with intelligent circuits.

A further drawback is if medicament delivery devices that are approved by national drug agencies and are out on the market were to be provided with added functionality built into the interior of the medicament delivery device. This would then require a new approval by the national drug agencies, which might take a number of years to obtain. It would be a better and simpler solution if the added functionality could be arranged outside the medicament delivery devices and not built into them.

One feature of particular interest in medicament delivery devices is to monitor the movement of components or elements of a drive unit, such as for example a plunger rod that is acting on a medicament container during delivery of a dose of medicament. However, since these components are arranged inside a housing of a medicament delivery device, access to them may be difficult without major modifications.

Document EP 2190506 discloses a medicament delivery device arranged with a monitoring unit. In one embodiment, the electronics unit is arranged as an attachable auxiliary device provided with a reader of RFID-sensors. One such RFID-sensor is comprised in a sensor system that is placed inside the medicament delivery device. Thus, this solution requires modification or insertion of additional components inside the medicament delivery device in order to obtain a higher degree of intelligence.

BRIEF DESCRIPTION OF INVENTION

In the present application, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

In the following description, the wording smart devices will be used. In this context, smart devices may include electronic devices that are provided with processors that are capable of running computer programs as well as storage space to store programs as well as data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further the smart devices may be provided with antennas for wireless communication with the networks. Also, the smart devices may be arranged with receiving and transmitting mechanisms capable of communicating with Near Range Wireless Communication circuits as well as programs capable of establishing and handling the communication with these circuits.

Further, in the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol-driven, gas, nebulizers having mouth or nasal pieces, dispensers for medicament in tablet form, eye dispensers, etc. The medicament delivery devices may be of either disposable type or re-usable type and may be provided with medicament containers suitably arranged for specific drugs in specific forms.

The aim of the present invention is to remedy the drawbacks of the state of the art devices. This aim is obtained with a medicament delivery device according to the features of the independent patent claim. Preferable embodiments of the invention form the subject of the dependent patent claims.

According to a main aspect of the invention, it comprises a medicament delivery device comprising a housing provided with a power unit. The power unit may comprise a drive force element; which drive force element may be arranged to act on an actuation element such as a plunger rod. The plunger rod may in turn be arranged to act on a stopper of a medicament container arranged in the housing.

The medicament delivery device may further comprise a monitoring unit, where the monitoring unit is detachably attached to the housing. Further at least one sensor may be arranged in the monitoring unit, where the at least one sensor is operably arranged to monitor the power unit for obtaining information regarding status of the medicament delivery device.

With this solution, the medicament delivery device does not have to be modified in any major way in order to obtain a monitoring function. Also, since the monitoring unit is detachable, it may be moved between different medicament delivery devices. Thus also disposable medicament delivery devices may be arranged with monitoring functions, which functions may be re-used many times by attaching and detaching the monitoring unit to different devices while discarding the disposable medicament delivery devices after use.

According to one aspect of the invention, the at least one sensor may comprise a force sensor arranged to monitor the force from the drive force element. In that respect, the medicament delivery device may further comprise a transfer element operably connected to the drive force element for transferring the force from the drive force element to the force sensor of the monitoring unit.

Measurement of the force from the drive force element is an advantage since force levels are quite straightforward to measure by for example piezo-electric force sensing elements. In order to be able to obtain information regarding the forces from the drive force element, the medicament delivery device may be arranged with a transfer element that can transfer the force from the interior of the housing to the outside.

As an alternative solution, the at least one sensor may comprise an optical sensor arranged to monitor the movement of the plunger rod. In this respect the housing may be arranged with an opening through which the optical sensor may monitor the movement of the plunger rod. The advantage with an optical sensor is that movement may be readily measured and is a technology that is well proven, e.g. optical mouse technologies. Further, no internal mechanical elements are needed for monitoring the inside a medicament delivery device, an opening is all that is required for allowing light from the optical sensor to enter the interior and to be reflected back out.

According to a favourable solution, the monitoring unit may further comprise a communication element for providing information to an external receiver. In this respect, the external receiver may be the user of the medicament delivery device, wherein the user may be provided with information regarding status of the medicament delivery device. This information may for example be that an injection sequence has started and/or that the injection sequence has ended and that it is safe to remove the medicament delivery device from the dose delivery site. Further in that respect, the communication element may comprise members for providing visual, audible and/or tactile information.

In addition, or as an alternative, the communication element may comprise a circuit for near range wireless communication such as NFC-, RFID-, ANT-, Zigbee- or Bluetooth technology. This provides the possibility to communicate and transfer information to for example smart devices, where the interfaces of the smart devices may be used for providing a user or other persons with status information of the medicament delivery device.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 1 is a schematic figure of a medicament delivery device according to one embodiment, FIG. 2 is a schematic figure of the medicament delivery device of FIG. 1 with a monitoring unit attached, FIG. 3 is an alternative embodiment of a monitoring unit arranged to a medicament delivery device.

DETAILED DESCRIPTION OF THE INVENTION

Figure 4:
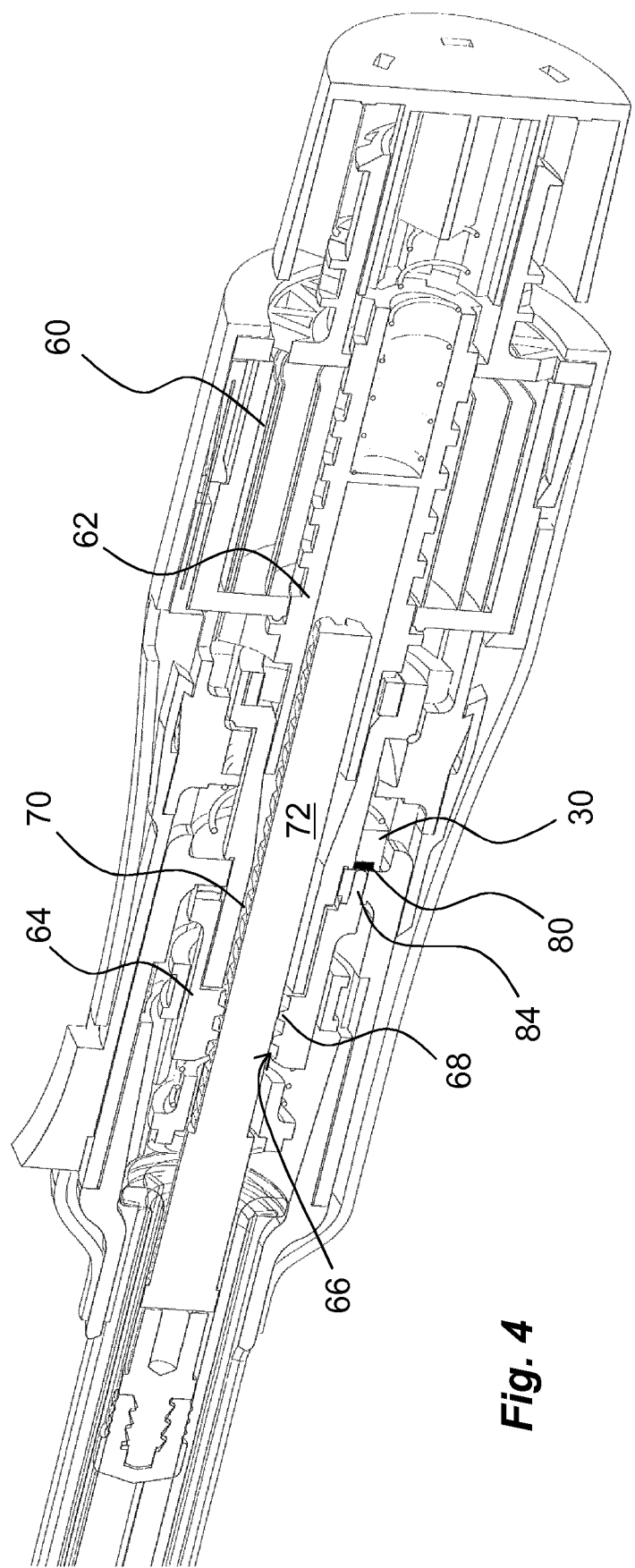
FIGS. 4-8 show a further embodiment of a medicament delivery device arranged with a monitoring unit.
Figure 6:
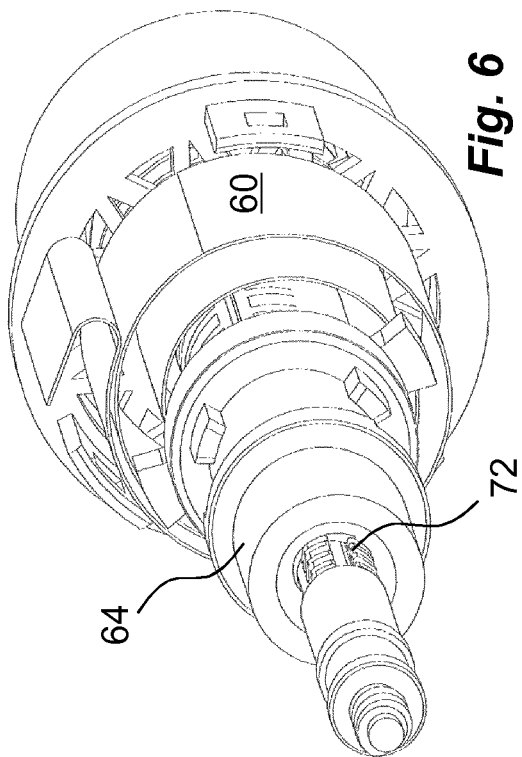
Figure 8:
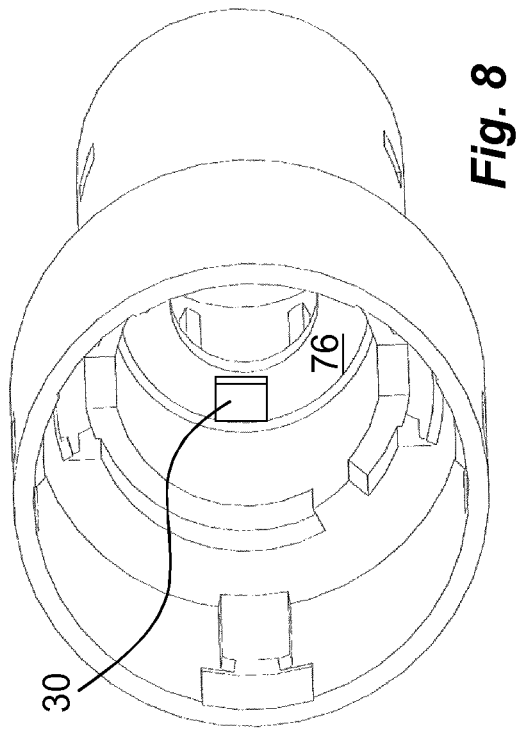

A device capable of sensing forces on components inside a medicament delivery device is shown in the figures. The medicament delivery device is preferably a disposable device that is to be discarded after use. The medicament delivery device comprises a housing 10 in which a transfer element 12 is arranged. The transfer element 12 is operably connected to components and functions of the medicament delivery device. In the embodiment shown the transfer element 12 has a generally disk-shaped body 14 that is arranged movable in a longitudinal direction in a recess 16 in a distal end wall 18 of the housing 10. A distally directed surface of the disk-shaped body 14 of the transfer element 12 is arranged with a pin 20 or the like protrusion that is positioned in a passage 22 in the distal end wall 18, whereby the pin 20 extends a distance outside the end wall 18 when the transfer element 12 is in its most distal position.

A drive unit may preferably be arranged in the medicament delivery device. The drive unit may comprise a drive force element such as a drive spring 24, which may be an injection sequence drive spring 24, has a distal end acting on a proximal surface of the disk-shaped body 14 of the transfer element 12. As seen in the embodiment, the drive spring 24 is acting on the transfer element 12 via a support disk 26 attached or integral to a distal end of a spring guide rod 28. In this respect, it is to be understood that the transfer element could be integrated with the support disk in that the disk-shaped body 14 is the same component as the support disk 26.

Thus, when the medicament delivery device is ready to be used, the drive spring 24 is tensioned and the transfer element 12 is forced to its most distal position with the pin 20 extending a distance outside the end wall 18. The proximal end of the drive spring is preferably operably connected to an actuation element such as a plunger rod 29, which in turn is capable of acting on a stopper of a medicament container such that when the drive spring is activated, the plunger rod is moved in the proximal direction, moving the stopper with it, thus performing a dose delivery sequence.

In order to obtain information regarding the use of the medicament delivery device a monitoring unit 30, FIG. 2, is arranged to the medicament delivery device. In the embodiment shown, the monitoring unit 30 is designed as an attachable unit having a housing 31 that can be releasably attached to the distal end of the medicament delivery device. For this purpose the monitoring unit 30 and the medicament delivery device are arranged with suitable attachment elements (not shown), which attachment elements could have a number of designs and configurations, such as for example threads, bayonet couplings, snap-in fittings etc.

The monitoring unit 30 is arranged with a force sensor 32 placed such that it is in contact with the pin 20 of the transfer element 12 when the monitoring unit 30 is attached to the medicament delivery device as seen in FIG. 2. In this respect the force sensor 32 may be of a design that can transform mechanical forces exerted on the force sensor 32 to some sort of electric signal or impulse, such as e.g. a piezo-electric sensor or a strain gauge. Further, the monitoring unit 30 may preferably be arranged with electronic circuits 34 to which the force sensor 32 is operably connected. In order to operate the electronics circuit 34, a suitable power source may be arranged, such as a button cell 36 or the like.

Further, the monitoring unit 30 may be arranged with suitable communication elements 38 for providing information to a user or to other persons that require information regarding the status of particular medicament delivery devices. In a basic embodiment, the monitoring unit 30 is arranged with a communication element in the form of a user interface 40 that may comprise visual displays and/or light sources and/or loudspeakers and/or tactile information providers such as vibrating elements.

In a further embodiment, the communication element of the monitoring unit may comprise some sort of wireless communication function, such as near range wireless communication technologies integrated in the electronics circuit. These may for instance be NFC-tags, RFID-tags, Ant-circuits, Zigbee-circuits, which are capable of transmitting information to external receivers over short distances. For instance, if NFC-tags are used, the monitoring unit may be operably connected to a smart device that is NFC-enabled. When such a smart device is held close to the monitoring unit, the NFC-tag may be energized and be made to transmit information to the smart device.

Another type of technology that may be used is Bluetooth. A large number of devices are capable of communicating with each other via Bluetooth technologies and an advantage is thereby that the medicament delivery device with the monitoring unit does not have to be very close to a receiver such as a smart device.

As mentioned above, the monitoring unit is arranged with a force sensor. The force sensor is capable of measuring the force from the drive spring via the transfer element. Thus, when for example an injection sequence is initiated by a user of the medicament delivery device, the force of the drive spring will move a stopper inside a medicament container, whereby a dose of medicament is delivered through a medicament delivery member attached to the medicament container. The movement of the stopper by the drive spring will cause the drive spring to extend in the longitudinal direction, whereby its deliverable force is gradually reduced. The changes in the force output from the drive spring is sensed by the force sensor, which may be used as information regarding the change of status or the progress of the medicament delivery device operation.

For example, when the force sensor detects a force that falls below a certain threshold, it may trigger a signal to the electronics. Further, the sensor may detect when the force starts to decrease as the plunger rod begins to move from a stationary state, indicating a start of a dose delivery sequence. Also, if the force sensor detects that the decrease in force from the drive spring has ended, due to a stop of the stopper at the end of the dose delivery operation, it may trigger a signal to the electronics. The electronics may then be programmed such that it will alert the user that it is safe to remove the medicament delivery device from the dose delivery site. Further information that the sensor may provide is the complete force curve during a complete dose delivery sequence. This force curve may be compared to force curves of pretested and normally functioning medicament containers to detect possible injection problems of the medicament delivery device such as siliconization problems or incomplete injections, e.g. due to internal friction of the medicament container exceeding the available spring force. The force curve may also indicate if the injection operation was made in air instead of in tissue, leading to different force curves.

FIG. 3 discloses a variant of the present invention. Here the medicament delivery device is arranged with an opening 50 providing access to the interior of the medicament delivery device and to components that are moving during operation of the medicament delivery device, such as for example a plunger rod 52 that during a dose delivery operation moves in the longitudinal direction by e.g. a drive spring, acting on the stopper of a medicament container for delivering a dose of medicament.

In this embodiment, the monitoring unit 30 may be arranged with an optical sensor 54 that is capable of providing a light beam 56 that is reflected back, detecting movement of components, such as the plunger rod 52 of the medicament delivery device which is moving during a dose delivery sequence. In this regard, the moving component may be arranged with suitable patterns, facilitating the detection of movement. The optical sensor 54 may, as mentioned above, be operably connected to an electronics circuit 34. In the same manner as above, the optical sensor may register the start of the movement, indicating e.g. a start of the dose delivery sequence as well as the stop of the movement, indicating a stop of the dose delivery sequence. Further the speed of the movement during the dose delivery sequence may be monitored and compared to movement patterns of pretested and normally functioning medicament container for detecting possible injection problems of the medicament delivery device.

FIGS. 4 to 8 show a further example of a medicament delivery device that may be arranged with a monitoring unit 30. In this embodiment, the medicament delivery device is arranged with a flat spiral spring 60 that is wound around a drive element 62 with an outer end attached to a housing part (not shown). The drive element 62 is operably connected to a drive nut 64 provided with a central passage 66 having threads 68. These threads 68 are arranged to cooperate with threads 70 on an outer surface of an elongated plunger rod 72. The drive nut 64 is further arranged with a distally directed support surface 74, FIG. 7, that is in contact with a proximally directed support wall 76, FIG. 5, of a chassis 78 of the medicament delivery device. During use the spiral spring 60 will rotate the drive element 62 and thus the drive nut 64. The rotation of the drive nut 64 will cause the plunger rod 72 to move in the proximal direction and to act on a medicament container for expelling a dose of medicament.

The action of the drive nut 64 on the plunger rod 72 will cause the drive nut 64 to be pressed against the support wall 76 with a certain force.

Figure 5:
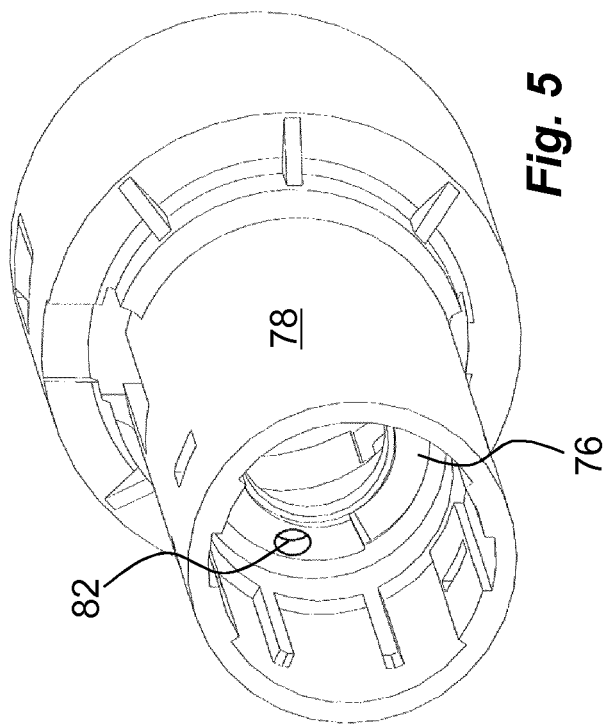
Figure 7:
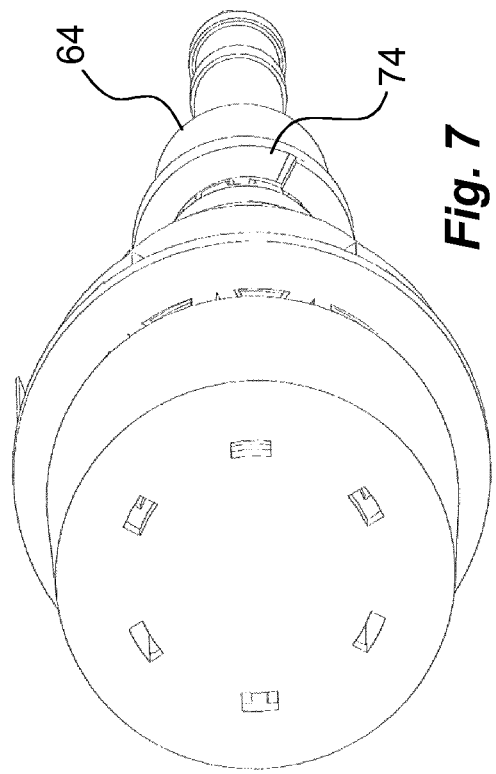

According to the invention a monitoring unit 30 may be arranged to the medicament delivery device, which monitoring unit is operably connected to a sensor 80, FIG. 4. In the embodiment shown the sensor 80 is a force sensor that is capable of sensing the force from the drive nut 64. In this case, a passage 82, FIG. 5, is arranged in the support wall 76. Further the drive nut 64 is arranged with a distally directed pin 84 that extends in the passage 82 of the support wall 76. The force sensor 80 is arranged on the opposite side of the support wall 76 such that a distal end of the pin 84 is in contact with the force sensor 80.

It is to be understood that the embodiments described above and shown in the drawings are to be regarded only as non-limiting examples of the invention and that it may be modified in many ways within the scope of the patent claims.

The invention claimed is:

1. A medicament delivery device comprising:
a housing;
an actuation element that is operably arranged to move inside the housing for expelling a dose of medicament;
a drive force element configured to act on the actuation element;
a monitoring unit detachably attached to the housing;
a sensor arranged in the monitoring unit, the sensor being operably arranged to monitor the drive force element for obtaining information regarding status of the medicament delivery device; and
a spring guide rod comprising a support disk on which the drive force element is supported.

2. The medicament delivery device according to claim 1, wherein the sensor is arranged to monitor a force from the drive force element.

3. The medicament delivery device according to claim 1, further comprising:
a transfer element operably connected to the drive force element for transferring a force from the drive force element to the sensor.

4. The medicament delivery device according to claim 1, wherein the support disk is integral with the spring guide rod.

5. The medicament delivery device according to claim 3, wherein the transfer element comprises a disk-shaped body.

6. The medicament delivery device according to claim 5, wherein the disk-shaped body of the transfer element comprises a protrusion.

7. The medicament delivery device according to claim 6, wherein the transfer element is arranged to be movable in a longitudinal direction in a recess in a distal end wall of the housing.

8. The medicament delivery device according to claim 7, wherein the protrusion is arranged in a passage in the distal end wall.

9. The medicament delivery device according to claim 8, wherein the protrusion is configured to extend a distance outside the distal end wall when the transfer element is in a most distal position.

10. The medicament delivery device according to claim 1, wherein the sensor comprises an optical sensor arranged to monitor movement of the actuation element.

11. The medicament delivery device according to claim 10, wherein the housing is arranged with an opening through which the optical sensor may monitor the movement of the actuation element.

12. The medicament delivery device according to claim 1, wherein the monitoring unit comprises a communication element configured for providing information to an external receiver.

13. The medicament delivery device according to claim 12, wherein the communication element comprises a member configured for providing visual information.

14. The medicament delivery device according to claim 12, wherein the communication element comprises a member configured for providing audible information.

15. The medicament delivery device according to claim 12, wherein the communication element comprises a member configured for providing tactile information.

16. The medicament delivery device according to claim 12, wherein the communication element comprises a circuit configured for near-range wireless communication.

17. The medicament delivery device according to claim 16, wherein the near-range wireless communication comprises NFC-, RFID-, ANT-, Zigbee- or Bluetooth technology.

18. A medicament delivery device comprising:
a housing,
a drive unit, said drive unit comprising:
an actuation element that is operably arranged to move inside the housing for expelling a dose of medicament;
a monitoring unit detachably attached to the housing;
at least one sensor arranged in the monitoring unit,
the at least one sensor being operably arranged to monitor the drive unit for obtaining information regarding status of the medicament delivery device,
wherein the drive unit comprises a drive force element acting on the actuation element,
wherein the at least one sensor comprises a force sensor arranged to monitor a force from the drive force element,
the medicament delivery device further comprising:
a transfer element operably connected to the drive force element for transferring the force from the drive force element to the force sensor of the monitoring unit; and
a spring guide rod comprising a support disk on which the drive force element is supported.

19. The medicament delivery device of claim 18, wherein the transfer element comprises a disk-shaped body.

20. The medicament delivery device of claim 19, wherein the disk-shaped body of the transfer element comprises a protrusion.

* * * * *